(12) United States Patent
Galli et al.

(10) Patent No.: US 7,589,201 B2
(45) Date of Patent: *Sep. 15, 2009

(54) DERIVATIVES OF 1,4-DIAZABICYCLO[3.2.1] OCTANECARBOXAMIDE, PREPARATION METHOD THEREOF AND USE OF SAME IN THERAPEUTICS

(75) Inventors: Frederic Galli, Vaucresson (FR); Odile LeClerc, Massy (FR); Alistair Lochead, Charenton le Pont (FR)

(73) Assignee: Sanofi-Aventis, Paris (FR)

( * ) Notice: Subject to any disclaimer, the term of this patent is extended or adjusted under 35 U.S.C. 154(b) by 171 days.

This patent is subject to a terminal disclaimer.

(21) Appl. No.: 11/456,345

(22) Filed: Jul. 10, 2006

(65) Prior Publication Data

US 2007/0155749 A1    Jul. 5, 2007

Related U.S. Application Data

(63) Continuation of application No. PCT/FR2005/000027, filed on Jan. 7, 2005.

(30) Foreign Application Priority Data

Jan. 16, 2004    (FR) .................... 04 00390

(51) Int. Cl.
C07D 487/04    (2006.01)
(52) U.S. Cl. .................... 544/349
(58) Field of Classification Search ............ 544/349
See application file for complete search history.

(56) References Cited

U.S. PATENT DOCUMENTS

| | | | |
|---|---|---|---|
| 2005/0182062 A1* | 8/2005 | Galli et al. | 514/249 |
| 2006/0052368 A1* | 3/2006 | Ernst et al. | 514/221 |
| 2007/0249588 A1* | 10/2007 | Ernst et al. | 514/218 |

FOREIGN PATENT DOCUMENTS

| | | |
|---|---|---|
| FR | 2845388 | 4/2004 |
| WO | WO 96/11929 | 4/1996 |
| WO | WO 99/42465 | 8/1999 |
| WO | WO 01/92261 | 12/2001 |
| WO | WO 03/044018 | 5/2003 |

* cited by examiner

*Primary Examiner*—Brenda L Coleman
(74) *Attorney, Agent, or Firm*—Balaram Gupta

(57) ABSTRACT

The invention relates to a compound of formula (I):

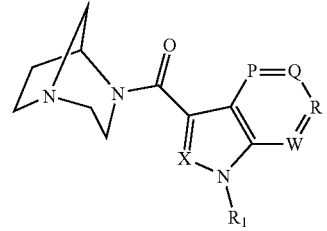

(I)

Wherein $R_1$, X, P, Q, R and W are as defined herein. The invention also relates to the use of same in therapeutics.

21 Claims, No Drawings

DERIVATIVES OF 1,4-DIAZABICYCLO[3.2.1] OCTANECARBOXAMIDE, PREPARATION METHOD THEREOF AND USE OF SAME IN THERAPEUTICS

CROSS REFERENCE TO RELATED APPLICATIONS

This application is a continuation of International application No. PCT/FR2005/000,027, Jan. 7, 2005, which is incorporated herein by reference in its entirety; which claims the benefit of priority of French Patent Application No. 04/00, 390, filed Jan. 16, 2004.

BACKGROUND OF THE INVENTION

Field of the Invention

The present invention relates to compounds which are nicotinic receptor ligands. They are useful in the treatment or prevention of disorders associated with dysfunction of nicotinic receptors.

SUMMARY OF THE INVENTION

The compounds of the invention conform to the general formula (I)

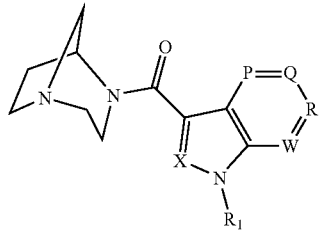

(I)

in which

X represents a nitrogen atom or a group of general formula C—$R_2$,

P, Q, R and W represent each independently of one another a nitrogen atom or a group of general formula C—$R_3$, $R_1$ represents a hydrogen atom or a ($C_1$-$C_6$)alkyl group, $R_2$ represents a ($C_1$-$C_6$)alkyl group, $R_3$ represents a hydrogen or halogen atom or a ($C_1$-$C_6$) alkyl, ($C_1$-$C_6$)alkoxy, nitro, amino, trifluoromethyl or cyano group or a group of general formula —$NR_4R_5$, —$NR_4C(=O)$ $R_5$, —$NR_4C(=O)NR_5R_6$, —$NR_4C(=O)OR_5$, $NR_4S(=O)_2$ $NR_5R_6$, —$OR_5$, —$OC(=O)R_5$, —$OC(=O)OR_5$, —$OC$ $(=O)ONR_4R_5$, —$OC(=O)SR_5$, —$C(=O)OR_5$, $C(=O)R_5$, —$C(=O)NR_4R_5$, $SR_5$, —$S(=O)R_5$, —$S(=O)_2R_5$ or —$S(=O)_2NR_4R_6$, or a phenyl group optionally substituted by one or more groups selected from halogen atoms and ($C_1$-$C_6$)alkyl, ($C_1$-$C_6$)alkoxy, nitro, amino, trifluoromethyl or cyano groups or groups of general formula —$NR_4R_5$, —$NR_4C(=O)R_5$, —$NR_4C(=O)NR_5R_6$, —$NR_4C(=O)$ $OR_5$, $NR_4S(=O)_2NR_5R_6$, —$OR_5$, —$OC(=O)R_5$, —$OC$ $(=O)OR_5$, —$OC(=O)ONR_4R_5$, —$OC(=O)SR_5$, —$C(=O)OR_5$, —$C(=O)NR_4R_5$, $SR_5$, —$S(=O)R_5$, —$S(=O)_2R_5$ or —$S(=O)_2NR_4R_6$, or $R_3$ represents a group selected from imidazole, pyridine, pyridazine, pyrimidine, pyrazole, pyrazine, triazole, quinoline, isoquinoline, tetrazole, furan, thiophene, thiazole, isothiazole, oxazole, isoxazole, pyrrole, tetrahydroquinoline, tetrahydroisoquinoline, indole, benzimidazole, benzofuran, dihydrobenzofuran, cinnoline, indazole, phthalazine, triazine, isoindole, oxadiazole, thiadiazole, furazan, benzofurazan, benzothiophene, dihydrobenzothiophene, benzotriazole, benzothiazole, benzisothiazole, benzoxazole, benzisoxazole, quinazoline, quinoxaline, naphthyridine, dihydroquinoline, dihydroisoquinoline, furopyridine, dihydrofuropyridine, pyrrolopyridine, thienopyridine, dihydrothienopyridine, imidazopyridine, pyrazolopyridine, oxazolopyridine, isoxazolopyridine, isoxazolopyridine, thiazolopyridine, isothiazolopyridine, pyrrolopyrimidine, furopyrimidine, dihydrofuropyrimidine, thienopyrimidine, dihydrothienopyrimidine, imidazopyrimidine, pyrazolopyrimidine, oxazolopyrimidine, isoxazolopyrimidine, thiazolopyrimidine, isothiazolopyrimidine, furopyrazine, dihydrofuropyrazine, pyrrolopyrazine, thienopyrazine, dihydrothienopyrazine, imidazopyrazine, pyrazolopyrazine, oxazolopyrazine, isoxazolopyrazine, thiazolopyrazine, isothiazolopyrazine, furopyridazine, dihydrofuropyridazine, pyrrolopyridazine, thienopyridazine, dihydrothienopyridazine, imidazopyridazine, pyrazolopyridazine, oxazolopyridazine, isoxazolopyridazine, thiazolopyridazine or isothiazolopyridazine ring systems, $R_4$, $R_5$ and $R_6$ represent each independently of one another a halogen atom or a linear or branched ($C_1$-$C_6$)alkyl, linear or branched ($C_2$-$C_6$)alkenyl or linear or branched ($C_2$-$C_6$)alkynyl group, or a ($C_3$-$C_8$)cycloalkyl, ($C_3$-$C_8$)cycloalkyl ($C_1$-$C_3$) alkyl, ($C_4$-$C_8$)cycloalkenyl or phenyl group, it being possible for the groups of general formulae $NR_4R_5$ and $NR_5R_6$ to form, with the nitrogen atom which carries them, a group selected from aziridinyl, azetidinyl, pyrrolidinyl, piperidinyl, azepinyl, piperazinyl, morpholinyl, thiomorpholinyl, pyrrolinyl, indolinyl, pyrazolinyl, pyrazolidinyl, imidazolinyl, 3H-indolyl, quinuclidinyl and quinolizinyl groups.

The compounds of the invention may exist in the form of bases or of addition salts with acids, of hydrates or of solvates.

DETAILED DESCRIPTION OF THE INVENTION

Since the diazabicyclooctane ring systems contain an asymmetric carbon atom, the compounds of the invention may exist in the form of pure enantiomers or of mixtures of enantiomers. The enantiomers may be separated by methods known to the skilled person, such as separation by fractional crystallization of diastereoisomeric salts of chiral acids, or separation by chromatography on a chiral support.

In accordance with the invention the compounds of general formula (I) may be prepared by a process which is illustrated by scheme 1 below. 1,4-Diazabicyclo[3.2.1]octane of formula (II) is reacted with a compound of general formula (III) in which X, P, Q, R, W and $R_1$ are as defined above in the presence of a coupling agent such as, for example, N,N'-carbonyldiimidazole in a solvent such as dimethylformamide. The carboxylic acid function present on the compound of general formula (III) may also be converted, in a prior step, into an acid chloride function, in order to react with the 1,4-diazabicyclo[3.2.1]octane in a solvent such as dichloroethane.

Scheme 1

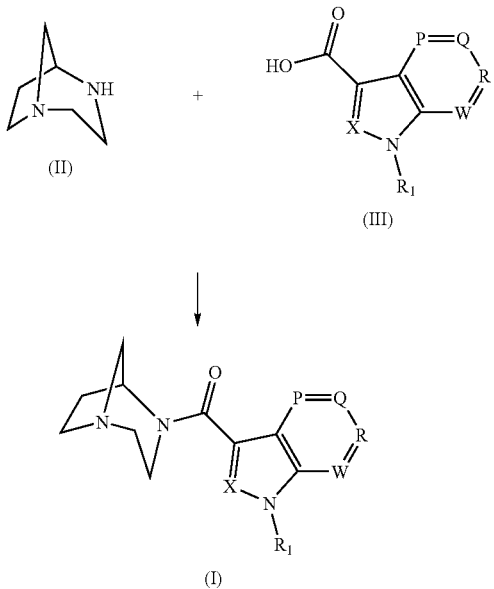

Alternatively the compounds of general formula (I) may be prepared by a process which is illustrated by scheme 2 below.

1,4-Diazabicyclo[3.2.1]octane of formula (II) is reacted with a compound of general formula (IV) in which X, P, Q, R, W and $R_1$ are as defined above and Z represents a bromine or iodine atom in the presence of carbon monoxide and a palladium catalyst such as, for example, bis(triphenylphosphino) dichloropalladium and of a base such as, for example, triethylamine in a solvent such as, for example, dimethylformamide.

Scheme 2

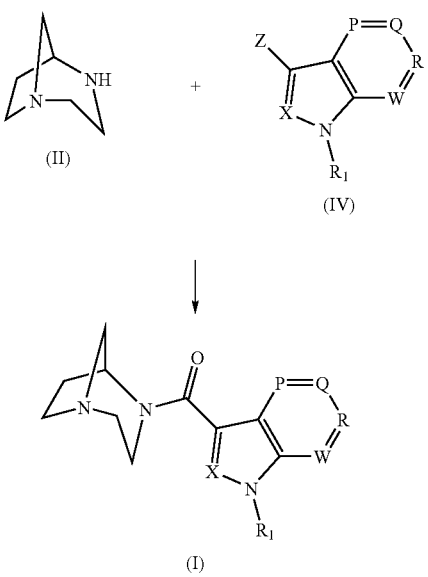

The compounds of general formula (III) are available commercially or are accessible by methods described in the literature, as for example in *Can. J. Chem.* 1988, 66, 420-8.

The compounds of general formula (IV) are available commercially or are accessible by methods described in the literature, as for example in *J. Het. Chem.* 1983, 475.

The preparation of 1,4-diazabicyclo[3.2.1]octane is described in *J. Med. Chem.* 1977, 20, 1333.

The examples below illustrate in detail the preparation of a number of compounds according to the invention. The elemental microanalyses and the IR and NMR spectra confirm the structures of the compounds obtained. The numbers of the compounds indicated between parentheses in the titles correspond to those of the table given later on. In the names of the compounds, the hyphen "-" forms part of the word, and the underscore mark "_" serves merely to indicate the line break; it should be deleted in the absence of a break, and should not be replaced with either a normal hyphen or a space.

EXAMPLE 1

Compound No. 2

3-(1,4-Diazabicyclo[3.2.1]oct-4-ylcarbonyl)-1H-indazole hydrochloride 1:1

A 50 ml reactor is charged with 0.165 g (1.02 mmol) of 1H-indazole-3-carboxylic acid and 1 ml of thionyl chloride and the mixture is heated at ref lux for 1 h 30 min and concentrated under reduced pressure. Then 1.2 ml of pyridine and 0.30 g (2.67 mmol) of 1,4-diazabicyclo[3.2.1]octane are added and the mixture is heated at reflux for 1 h 30 min.

The solvent is evaporated off under reduced pressure and the residue is taken up in 1 ml of chloroform and purified by chromatography on a silica gel column, eluting with a 70/30/3 mixture of ethyl acetate, methanol and aqueous ammonia.

This gives 0.16 g of product, which is dissolved in 10 ml of acetone before addition of 0.47 ml of a 5N solution of hydrochloric acid in isopropyl alcohol. The crystals obtained (0.17 g) are collected by filtration and dried under reduced pressure.

Melting point: 286-287° C.

EXAMPLE 2

Compound No. 3

6-Chloro-3-(1,4-diazabicyclo[3.2.1]oct-4-ylcarbonyl)-1H-indazole hydrobromide 1:1

A 10 ml reactor is charged in succession with 0.25 g (0.9 mmol) of 3-iodo-6-chloro-1H-indazole, 0.09 g (0.13 mmol) of bis(triphenylphosphino)-dichloro-palladium, 0.25 g (2.24 mmol) of 1,4-diazabicyclo[3.2.1]octane and 0.31 ml (2.24 mmol) of triethylamine in solution in 1 ml of dimethylformamide. The mixture is subsequently purged with carbon monoxide and heated at 70° C. for 8 h. The reaction mixture is poured into 10 ml of saturated aqueous ammonium chloride solution and the aqueous phase is extracted with chloroform. The organic phases are dried, filtered and concentrated under reduced pressure. The residue is purified by chromatography on a silica gel column, eluting with a 90/10/1 mixture of chloroform, methanol and aqueous ammonia.

This gives 0.2 g of product, which is dissolved in 1 ml of isopropyl alcohol before addition of 0.13 ml of a 5N solution of hydrochloric acid in isopropyl alcohol. The crystals obtained (0.076 g) are collected by filtration and dried under reduced pressure.

Melting point: 285-286° C.

EXAMPLE 3

Compound No. 1

3-(1,4-Diazabicyclo[3.2.1]oct-4-ylcarbonyl)-6-methyl-1H-pyrazolo[3,4-b]pyridine hydrobromide 2:1

By analogy with Example 2, 0.7 g (3.3 mmol) of 3-bromo-6-methyl-1H-pyrazolo[3,4-b]pyridine is reacted with 1.1 g (9.9 mmol) of 1,4-diazabicyclo[3.2.1]octane in the presence of 0.35 g (0.5 mmol) of bis(triphenylphosphino)dichloropalladium and 2.3 ml of triethylamine in 10 ml of dimethylformamide under the conditions described for Example 1, giving 0.21 g of product, which is dissolved in 20 ml of acetone before addition of 0.27 ml of a 5.7 N solution of hydrobromic acid in acetic acid. The dihydrobromide crystals are collected by filtration and dried under vacuum.

Melting point: 290-291° C.

EXAMPLE 4

Compound No. 4

3-(1,4-Diazabicyclo[3.2.1]oct-4-ylcarbonyl)-5-fluoro-1H-indazole hydrobromide 2:1

By analogy with Example 2, 0.23 g (0.88 mmol) of 3-iodo-5-fluoro-1H-indazole is reacted with 0.25 g (2.19 mmol) of 1,4-diazabicyclo[3.2.1]octane in the presence of 0.092 g (0.13 mmol) of bis(triphenylphosphino)dichloropalladium and 0.3 ml of triethylamine in 1 ml of dimethylformamide under the conditions described for Example 2. This gives 0.136 g of product, which is dissolved in 20 ml of acetone before addition of 0.18 ml of a 5.7 N solution of hydrobromic acid in acetic acid. The hydrobromide crystals are collected by filtration and dried under vacuum.

Melting point: 283-284° C.

The table below illustrates the chemical structures and the physical properties of a number of compounds of the invention.

In the column "Q", "Me" denotes a methyl group and "Ms" denotes a methanesulfonyl group.

In the column "St.", "(+/−)" denotes a racemate, and "(+)" and "(−)" denote the dextrorotatory and levorotatory enantiomers, respectively.

In the "Salt" column, "−" denotes a compound in base form, "HBr" denotes a hydrobromide, "HCl" denotes a hydrochloride and "ox." denotes an oxalate, or ethanedioate.

TABLE

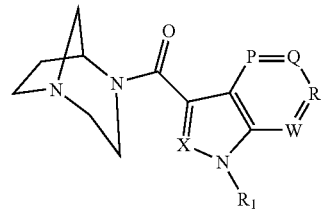

(I)

| No. | X | P | Q | R | W | $R_1$ | St. | Salt | m.p. (° C.) |
|---|---|---|---|---|---|---|---|---|---|
| 1 | N | CH | CH | C—$CH_3$ | N | H | (+/−) | HBr | 290-291 |
| 2 | N | CH | CH | CH | CH | H | (+/−) | HCl | 286-287 |
| 3 | N | CH | CH | C—Cl | CH | H | (+/−) | HBr | 285-286 |
| 4 | N | CH | C—F | CH | CH | H | (+/−) | HBr | 283-284 |
| 5 | N | CH | CH | C—$CH_3$ | CH | H | (+/−) | HBr | 299-300 |
| 6 | N | CH | C—OMs | CH | CH | H | (+/−) | ox. | 272-273 |
| 7 | N | CH | C—Cl | CH | CH | H | (+/−) | — | 240-241 |
| 8 | N | CH | C—OMe | CH | CH | H | (+/−) | — | 168-170 |
| 9 | N | CH | CH | CH | N | H | (+/−) | ox. | 210-211 |
| 10 | N | CH | CH | C—$CH_3$ | N | H | $[\alpha]_D^{20} + -73.9$ (c = 0, 8 MeOH) | HCl | 327-329 |
| 11 | N | CH | CH | C—$CH_3$ | N | H | $[\alpha]_D^{20} + +70.2$ (c = 1, 8 MeOH) | HCl | 328-330 |

The compounds of the invention were subjected to pharmacological tests, which demonstrated their advantage as active substances of medicaments.

For instance, they were studied with regard to their affinity for nicotinic receptors containing the $\alpha_4\beta_2$ subunit in accordance with the methods described by Anderson and Arneric in *Eur. J. Pharmacol.* 1994, 253, 261 and by Hall et al. in *Brain Res.* 1993, 600, 127. Male Sprague Dawley rats weighing 150 to 200 g are decapitated and the whole brain is removed rapidly, homogenized in 15 volumes of 0.32 M sucrose solution at 40° C. and then centrifuged at 1000 G for 10 min. The pellet is discarded and the supernatant is centrifuged at 20,000 G at 4° C. for 20 min. The pellet is recovered and homogenized using a Polytron™ mill in 15 volumes of double-distilled water at 4° C., then centrifuged at 8,000 G for 20 min. The pellet is discarded and the supernatant and the layer of skin (buffy coat) are centrifuged at 40 000 G for 20 min, and the pellet is recovered, resuspended in 15 ml of double-distilled water and centrifuged again at 40,000 G, before being stored at −80° C.

On the day of the experiment the tissue is slowly thawed and is suspended in 3 volumes of buffer. 150 μl of this membrane suspension are incubated at 4° C. for 120 min in the presence of 100 μl of 1 nM [$^3$H]-cytisine in a final volume of 500 μl of buffer, in the presence or absence of test compound. The reaction is stopped by filtration on Whatman GF/B™ filters pretreated with polyethyleneimine, the filters are rinsed with twice 5 ml of buffer at 4° C. and the radioactivity retained on the filter is measured by liquid scintigraphy. The non-specific binding is determined in the presence of 10 μM (−)-nicotine; the nonspecific binding represents 75% to 85% of the total binding recovered on the filter. For each concentration of compound studied, the percentage inhibition of the specific binding of [$^3$H]-cytisine is determined, after which the $IC_{50}$ is calculated, which is the concentration of compound that inhibits 50% of the specific binding.

The $IC_{50}$ values of the compounds of the invention having the greatest affinity are situated between 1 and 10 μM.

The compounds of the invention were also studied with regard to their affinity for nicotinic receptors containing the $\alpha_7$ subunit, in accordance with the methods described by Mark and Collins in *J. Pharmacol. Exp. Ther.* 1982, 22, 564 and by Marks et al. in *Mol. Pharmacol.* 1986, 30, 427.

Male OFA rats weighing 150 to 200 g are decapitated, the whole brain is removed rapidly and is homogenized using a Polytron™ mill in 15 volumes of 0.32 M sucrose solution at 4° C., then centrifuged at 1,000 G for 10 min. The pellet is discarded and the supernatant is centrifuged at 8,000 G at 4° C. for 20 min. The pellet is recovered and is homogenized using a Polytron™ mill in 15 volumes of double-distilled water at 4° C., then centrifuged at 8,000 G for 20 min. The pellet is discarded and the supernatant and layer of skin (buffy coat) are centrifuged at 40,000 G for 20 min. The pellet is recovered and resuspended in 15 volumes of double-distilled water at 4° C. and is centrifuged again at 40,000 G for 20 min, before being stored at −80° C. On the day of the experiment, the tissue is slowly thawed and is suspended in 5 volumes of buffer. 150 μl of this membrane suspension are preincubated at 37° C. for 30 min, in the dark, in the presence or absence of the test compound. The membranes are then incubated at 37° C. for 60 min, in the dark, in the presence of 50 μl of 1 nM [$^3$H]-α-bungarotoxin in a final volume of 250 μl of 20 mM HEPES, 0.05% polyethyleneimine buffer. The reaction is stopped by filtration on Whatman GF/C™ filters pretreated for 3 h with 0.05% polyethylene-imine. The filters are rinsed with two times 5 ml of buffer at 4° C. and the radioactivity retained on each filter is measured by liquid scintigraphy. The nonspecific binding in the presence of α-bungarotoxin at 1 μM final is measured; the nonspecific binding represents approximately 60% of the total binding recovered on the filter. For each concentration of compound studied, the percentage inhibition of the specific binding of [$^3$H]-α-bungarotoxin is measured and then the $IC_{50}$ is calculated, the concentration of compound that inhibits 50% of the specific binding. The $IC_{50}$ values of the compounds of the invention which have the greatest affinity are situated between 0.010 and 0.10 μM.

The $IC_{50}$ values of some specific compounds are indicated in the table below.

| Compound No. | $IC_{50}\ \alpha_7$ μM | $IC_{50}\ \alpha_4\beta_2$ |
|---|---|---|
| 1 | 0.056 | >10 |
| 4 | 0.055 | — |
| 7 | 0.224 | — |

The above results show that the compounds of the invention are selective ligands for the $\alpha_7$ subunits of the nicotinic receptor.

The results of the various tests suggest the use of the compounds in the treatment or prevention of disorders associated with dysfunction of the nicotinic receptors, particularly within the central nervous system.

These disorders include cognitive impairment, more specifically memory impairment, but also attention impairment, which are associated with Alzheimer's disease, pathological aging (Age Associated Memory Impairment, AAMI), Parkinson's disease, trisomy 21 (Down's syndrome), Korsakoff's alcoholic syndrome, and vascular dementia (multi-infarct dementia, MDI).

The compounds of the invention might also be useful in the treatment of motor disorders observed in Parkinson's disease or other neurological diseases, such as Huntington's chorea, Tourette's syndrome, tardive dyskinesia, and hyperkinesias.

The compounds of the invention may also constitute a curative or symptomatic treatment for cerebrovascular accidents and cerebral hypoxic episodes. They may be used in cases of psychiatric pathologies: schizophrenia, depression, anxiety, panic attacks, and obsessive compulsive behaviors.

They may prevent the symptoms caused by withdrawal from tobacco, from alcohol, and from various substances that induce a dependency, such as cocaine, LSD, cannabis and benzodiazepines.

Furthermore, the compounds of the invention may also be used for the treatment of lower limb ischemia, obliterative arteritis of the lower limbs (PAD: peripheral arterial disease), cardiac ischemia (stable angina), myocardial infarction, cardiac insufficiency, cutaneous cicatrization deficiency in diabetic patients, and varicose ulcers of venous insufficiency.

For each of the aforementioned pathologies, treatment may be performed with the nicotinic agent alone and/or in combination with the reference medicaments indicated in the pathology.

Consequently the present invention additionally provides pharmaceutical compositions containing an effective dose of at least one compound according to the invention, in base form or in the form of a salt or solvate which is pharmaceutically acceptable, and in a mixture, where appropriate, with suitable excipients.

The said excipients are selected according to the pharmaceutical form and mode of administration desired.

The pharmaceutical compositions according to the invention may thus be intended for oral, sublingual, subcutaneous, intramuscular, intravenous, topical, intratracheal, intranasal, transdermal, rectal or intraocular administration.

The unit forms of administration may be, for example, tablets, gel capsules, granules, powders, oral or injectable solutions or suspensions, transdermal patches, or suppositories. For topical administration consideration may be given to ointments, lotions, and eye drops.

The said unit forms are dosed to allow a daily administration of 0.01 to 20 mg of active principle per kg of body weight, depending on the pharmaceutical form.

To prepare tablets, the active principle, in micronized form or otherwise, is admixed with a pharmaceutical vehicle, which may be composed of diluents, such as, for example, lactose, microcrystalline cellulose, starch, and formulation adjuvants such as binders (polyvinylpyrrolidone, hydroxypropylmethylcellulose, etc.), glidants, such as silica, lubricants, such as magnesium stearate, stearic acid, glycerol tribehenate, and sodium stearylfumarate. Wetting agents or surfactants such as sodium lauryl sulfate may also be added.

The production techniques may include art recognized techniques such as, direct tableting, dry granulation, wet granulation or hot melting.

The tablets may be plain, coated, for example with sucrose, or enveloped with various polymers or other appropriate materials. They may be designed in order to allow rapid, delayed or sustained release of the active principle by virtue of polymeric matrices or of specific polymers used in the covering.

To prepare gel capsules, the active principle is mixed with dry pharmaceutical vehicles (simple mixing, dry or wet granulation, or hot melting), or with liquid or semisolid pharmaceutical vehicles.

The gel capsules may be hard or soft, and may be film-coated or not, so as to exhibit rapid, sustained or delayed activity (for an enteric form, for example).

A composition in the form of a syrup or elixir or for administration in the form of drops may contain the active principle together with a sweetener, preferably a calorie-free sweetener, methylparaben or propylparaben as an antiseptic, a flavor enhancer, and a dye.

Water-dispersible granules and powders may contain the active principle mixed with dispersants or wetting agents, or with dispersants such as polyvinylpyrrolidone, and also with sweeteners and taste corrigents.

For rectal administration, suppositories are employed which are prepared with binders that melt at the rectal temperature, such as cocoa butter or polyethylene glycols, for example.

For parenteral administration, use is made of aqueous suspensions, isotonic saline solutions or sterile injectable solutions containing pharmacologically compatible dispersants and/or wetting agents, such as propylene glycol or butylene glycol, for example.

The active principle may also be formulated in the form of microcapsules, where appropriate with one or more vehicles or additives, or else with a polymeric matrix or with a cyclodextrin (transdermal patches, sustained-release forms).

The topical compositions according to the invention comprise a medium which is compatible with the skin. They may in particular be in the form of aqueous, alcoholic or aqueous-alcoholic solutions, gels, water-in-oil or oil-in-water emulsions having the appearance of a cream or gel, microemulsions or aerosols, or else in the form of vesicular dispersions containing ionic and/or nonionic lipids. These pharmaceutical forms are prepared according to the usual methods in the fields under consideration.

Finally, the pharmaceutical compositions according to the invention may contain, in addition to a compound of general formula (I), other active principles which may be useful in the treatment of the disorders and diseases indicated above.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A compound of the formula (I)

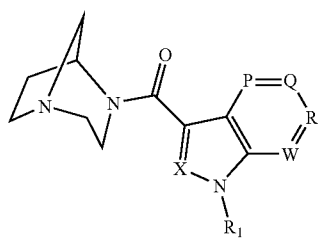

(I)

wherein
X is nitrogen;
P, Q, R and W, each independently of one another, are nitrogen or C—$R_3$;
$R_1$ is hydrogen or ($C_1$- $C_6$)alkyl; and
$R_3$ is hydrogen, halogen, ($C_1$- $C_6$)alkoxy, ($C_1$- $C_6$)alkoxy, nitro, amino, trifluoromethyl, cyano,
or a racemate or an enantiomer thereof, or a salt thereof.

2. The compound according to claim 1, which is selected from:
   3-(1,4-diazabicyclo[3.2.1]oct-4-ylcarbonyl)-6-methyl-1H-pyrazolo[3,4-b]pyridine;
   3-(1,4-diazabicyclo[3.2.1]oct-4-ylcarbonyl)-1H-indazole;
   6-chloro-3-(1,4-diazabicyclo[3.2.1]oct-4-ylcarbonyl)-1H-indazole;
   3-(1,4-diazabicyclo[3.2.1]oct-4-ylcarbonyl)-5-fluoro-1H-indazole;
   3-(1,4-diazabicyclo[3.2.1]oct-4-ylcarbonyl)-6-methyl-1H-indazole;
   5-chloro-3-(1,4-diazabicyclo[3.2.1]oct-4-ylcarbonyl)-1H-indazole;
   3-(1,4-diazabicyclo[3.2.1]oct-4-ylcarbonyl)-5-methoxy-1H-indazole;
   3-(1,4-diazabicyclo[3.2.1]oct-4-ylcarbonyl)-1H-pyrazolo[3,4-b]pyridine;
   (+)3-(1,4-diazabicyclo[3.2.1]oct-4-ylcarbonyl)-6-methyl-1H-pyrazolo[3,4-b]pyridine; and
   (−)3-(1,4-diazabicyclo[3.2.1]oct-4-ylcarbonyl)-6-methyl-1H-pyrazolo[3,4-b]pyridine; or
   a racemate or an enantiomer thereof, or a salt thereof.

3. The compound according to claim 1, which is selected from:
   3-(1,4-diazabicyclo[3.2.1]oct-4-ylcarbonyl)-6-methyl-1H-pyrazolo[3,4-b]pyridine hydrobromide;
   3-(1,4-diazabicyclo[3.2.1]oct-4-ylcarbonyl)-1H-indazole hydrochloride;
   6-chloro-3-(1,4-diazabicyclo[3.2.1]oct-4-ylcarbonyl)-1H-indazole hydrobromide;
   3-(1,4-diazabicyclo[3.2.1]oct-4-ylcarbonyl)-5-fluoro-1H-indazole hydrobromide;
   3-(1,4-diazabicyclo[3.2.1]oct-4-ylcarbonyl)-6-methyl-1H-indazole hydrobromide;
   3-(1,4-diazabicyclo[3.2.1]oct-4-ylcarbonyl)-1H-pyrazolo[3,4-b]pyridine oxalate;
   (+)3-(1,4-diazabicyclo[3.2.1]oct-4-ylcarbonyl)-6-methyl-1H-pyrazolo[3,4-b]pyridine hydrochloride; and
   (−)3-(1,4-diazabicyclo[3.2.1]oct-4-ylcarbonyl)-6-methyl-1H-pyrazolo[3,4-b]pyridine hydrochloride; or
   a racemate or an enantiomer thereof.

4. The compound according to claim 1, which is selected from:
   3-(1,4-diazabicyclo[3.2.1]oct-4-ylcarbonyl)-6-methyl-1H-pyrazolo[3,4-b]pyridine;
   3-(1,4-diazabicyclo[3.2.1]oct-4-ylcarbonyl)-5-fluoro-1H-indazole; and
   5-chloro-3-(1,4-diazabicyclo[3.2.1]oct-4-ylcarbonyl)-1H-indazole; or
   a racemate or an enantiomer thereof, or a salt thereof.

5. The compound according to claim 1, which is selected from:
   3-(1,4-diazabicyclo[3.2.1]oct-4-ylcarbonyl)-6-methyl-1H-pyrazolo[3,4-b]pyridine hydrobromide; and
   3-(1,4-diazabicyclo[3.2.1]oct-4-ylcarbonyl)-5-fluoro-1H-indazole hydrobromide; or
   a racemate or an enantiomer thereof.

6. A pharmaceutical composition comprising a compound according to claim 1 in combination with an excipient.

7. A pharmaceutical composition comprising a compound according to claim 2 in combination with an excipient.

8. A pharmaceutical composition comprising a compound according to claim 3 in combination with an excipient.

9. A pharmaceutical composition comprising a compound according to claim 4 in combination with an excipient.

10. A pharmaceutical composition comprising a compound according to claim 5 in combination with an excipient.

11. A method of treatment of a disorder in a patient comprising administering to said patient a therapeutically effective amount of a compound according to claim 1 or a racemate or an enantiomer thereof or a pharmaceutically acceptable salt thereof, wherein said disorder is selected from the group consisting of cognitive or attention impairment, motor disorder, anxiety, depression and symptoms caused by withdrawal from tobacco, alcohol, cocaine, LSD, cannabis and benzodiazepines.

12. The method according to claim 11, wherein said compound is selected from:
- 3-(1,4-diazabicyclo[3.2.1]oct-4-ylcarbonyl)-6-methyl-1H-pyrazolo[3,4-b]pyridine;
- 3-(1,4-diazabicyclo[3.2.1]oct-4-ylcarbonyl)-1H-indazole;
- 6-chloro-3-(1,4-diazabicyclo[3.2.1]oct-4-ylcarbonyl)-1H-indazole;
- 3-(1,4-diazabicyclo[3.2.1]oct-4-ylcarbonyl)-5-fluoro-1H-indazole;
- 3-(1,4-diazabicyclo[3.2.1]oct-4-ylcarbonyl)-6-methyl-1H-indazole;
- 5-chloro-3-(1,4-diazabicyclo[3.2.1]oct-4-ylcarbonyl)-1H-indazole;
- 3-(1,4-diazabicyclo[3.2.1]oct-4-ylcarbonyl)-5-methoxy-1H-indazole;
- 3-(1,4-diazabicyclo[3.2.1]oct-4-ylcarbonyl)-1H-pyrazolo[3,4-b]pyridine;
- (+)3-(1,4-diazabicyclo[3.2.1]oct-4-ylcarbonyl)-6-methyl-1H-pyrazolo[3,4-b]pyridine; and
- (−)3-(1,4-diazabicyclo[3.2.1]oct-4-ylcarbonyl)-6-methyl-1H-pyrazolo[3,4-b]pyridine; or a racemate or an enantiomer thereof, or a salt thereof.

13. The method according to claim 11, wherein said compound is selected from:
- 3-(1,4-diazabicyclo[3.2.1]oct-4-ylcarbonyl)-6-methyl-1H-pyrazolo[3,4-b]pyridine;
- 3-(1,4-diazabicyclo[3.2.1]oct-4-ylcarbonyl)-5-fluoro-1H-indazole; and
- 5-chloro-3-(1,4-diazabicyclo[3.2.1]oct-4-ylcarbonyl)-1H-indazole; or a racemate or an enantiomer thereof, or a salt thereof.

14. The method according to claim 11, wherein said disorder is cognitive or attention impairment.

15. The method according to claim 14, wherein said cognitive or attention impairment is selected from Alzheimer's disease, pathological aging (Age Associated Memory Impairment, AAMI), Parkinson's disease, trisomy 21 (Down's syndrome), Korsakoff's alcoholic syndrome, and vascular dementia (multi-infarct dementia, MDI).

16. The method according to claim 11, wherein said disorder is motor disorder.

17. The method according to claim 16, wherein said motor disorder is selected from Parkinson's disease, Huntington's chorea, Tourette's syndrome, tardive dyskinesia and hyperkinesias.

18. The method according to claim 11, wherein said disorder is anxiety.

19. The method according to claim 11, wherein said disorder is depression.

20. The method according to claim 11, wherein said disorder is symptoms caused by withdrawal from tobacco or alcohol.

21. A compound selected from the group consisting of:
- 3-(1,4-diazabicyclo[3.2.1]oct-4-ylcarbonyl)-1H-indazole-5-mesylate; and
- 3-(1,4-diazabicyclo[3.2.1]oct-4-ylcarbonyl)-1H-indazole-5-mesylate oxalate.

* * * * *

UNITED STATES PATENT AND TRADEMARK OFFICE
CERTIFICATE OF CORRECTION

| | | |
|---|---|---|
| PATENT NO. | : 7,589,201 B2 | Page 1 of 1 |
| APPLICATION NO. | : 11/456345 | |
| DATED | : September 15, 2009 | |
| INVENTOR(S) | : Frederic Galli et al. | |

It is certified that error appears in the above-identified patent and that said Letters Patent is hereby corrected as shown below:

In column 4, line 27, delete "ref lux" and insert -- reflux --, therefor.

In column 6, line 32, delete "+-" and insert -- =- --, therefor.

In column 6, line 34, delete "++" and insert -- =+ --, therefor.

In column 6, line 50, delete "40° C." and insert -- 4° C. --, therefor.

In column 7, line 36, delete "polyethylene-imine." and insert -- polyethyleneimine. --, therefor.

In column 10, line 2, in Claim 1, after "halogen," delete "($C_1$-$C_6$)alkoxy," and insert -- ($C_1$-$C_6$)alkyl, --, therefor.

Signed and Sealed this
Ninth Day of August, 2011

David J. Kappos
*Director of the United States Patent and Trademark Office*